(12) United States Patent
Dubowchik et al.

(10) Patent No.: US 6,908,931 B2
(45) Date of Patent: Jun. 21, 2005

(54) TETRAHYDROISOQUINOLINE DERIVATIVES AS MELATONIN $MT_2$ ANTAGONISTS

(75) Inventors: Gene M. Dubowchik, Middlefield, CT (US); Jonathan L. Ditta, Middletown, CT (US); Stephen R. Bertenshaw, Cheshire, CT (US)

(73) Assignee: Bristol-Myers Squibb Company, Princeton, NJ (US)

( * ) Notice: Subject to any disclaimer, the term of this patent is extended or adjusted under 35 U.S.C. 154(b) by 10 days.

(21) Appl. No.: 10/812,245

(22) Filed: Mar. 29, 2004

(65) Prior Publication Data

US 2004/0235891 A1 Nov. 25, 2004

Related U.S. Application Data

(60) Provisional application No. 60/461,977, filed on Apr. 10, 2003.

(51) Int. Cl.$^7$ .................. C07D 217/00; A61K 31/47
(52) U.S. Cl. ........................ 514/307; 546/146
(58) Field of Search .................... 546/146; 514/307

(56) References Cited

U.S. PATENT DOCUMENTS

| | | | |
|---|---|---|---|
| 3,132,147 A | * | 5/1964 | Schopf et al. ............... 546/96 |
| 3,922,285 A | | 11/1975 | Leimgruber et al. |
| 5,124,337 A | | 6/1992 | Dugar et al. |
| 5,362,736 A | | 11/1994 | Ishikawa et al. |

FOREIGN PATENT DOCUMENTS

| | | |
|---|---|---|
| DE | 2214498 | 10/1972 |
| EP | 501693 A1 | 9/1992 |

OTHER PUBLICATIONS

T. Itoh, et al, "Asymmetric Addition of Nucleophiles to C–1 Position of Isoquinolines Using (S)–Alanine Derivatives as Chiral Auxiliaries," TETRAHEDRON, 57, pp 8827–8839, 2001.

I. Osante, et al, "Stereodivergent Synthesis of Hetero–Fused Isoquinolines by Acyliminium and Metallation Methods," Eur. J. Org. Chem., 7, pp 1267–1277, 2001.

A.P. Venkov, et al, "Synthesis of 2–Acyl–1–Benzyl–, 1–Phenylethyl– and Spirobenzyltetrahydroisoquinolines," Synth. Communications, 26(4), pp 755–762, 1996.

Z. Czarnocki, et al, "(R)–2–Alkoxycarbonyl–1–Formyl–1,2,3,4–Tetrahydro–6,7–Dimethoxyisoquinolines from D–(–)–Tartaric Acid: Synthesis of (S)–Homolaudanosine and (S)–2,3,9,10,11–Pentamethoxyhomoprotoberberine," J. Chem. Soc., Chem. Commun., 7, pp 493–494, 1987.

Z. Czarnocki, et al, "Enantioselective Synthesis of Isoquinoline Alkaloids: Phenylethylisoquinoline and Aporphine Alkaloids," Can. J. Chem., 65, pp 2356–2361, 1987.

J.P. Marino, et al, "Selective Catechol Oxidations with Diphenyl Selenoxide. Applications to Phenolic Coupling," Tetrahedron Lett., 35, pp 3253–3256, 1979.

S. Morris Kupchan, et al, "Efficient Intramolecular Monophenol Oxidative Coupling," J. Org. Chem., 43(21), pp 4076–4081, 1978.

S. Morris Kupchan, et al, "New Biogenetic–Type Approach to Cephalotaxus Alkaloids and the Mechanism of Schelhammera–Type Homoerythrinadienone Formation in Vitro," J. Org. Chem., 43(23), pp 4464–4468, 1978.

S. Morris Kupchan, et al, "New Biogenetic–Type Approach to Cephalotaxus Alkaloids," J. Chem. Soc., Chem. Commun., 23, pp 847–848, 1977.

S. Morris Kupchan, et al, "Intramolecular Nonphenol Oxidative Coupling of Phenethylisoquinolines," J. Org. Chem., 43(12), pp 2521–2529, 1978.

S. Morris Kupchan, et al, "Efficient Intramolecular Monophenol Oxidative Coupling," J .Org. Chem., 41(25), pp 4049–4050, 1976.

S. Morris Kupchan, et al, "Novel Nonphenol Oxidative Coupling of Phenethylisoquinolines," J. Org. Chem., 41(25), pp 4047–4049, 1976.

J.P. Marino, et al, "The Chemistry of Prohomoerythrinadienone I.," Tetrahedron Lett., 46, pp 4553–4556, 1973.

* cited by examiner

*Primary Examiner*—Zinna Northington Davis
(74) *Attorney, Agent, or Firm*—James Epperson

(57) ABSTRACT

The invention encompasses a series of tetrahydroisoquinolines of formula I which are antagonists of the human melatonin $MT_2$ receptor and are useful as chronobiotic and sleep agents.

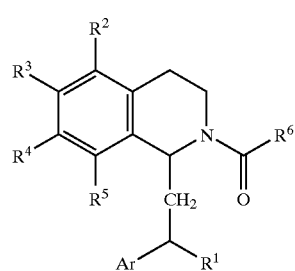

8 Claims, No Drawings

TETRAHYDROISOQUINOLINE DERIVATIVES AS MELATONIN MT$_2$ ANTAGONISTS

REFERENCE TO RELATED APPLICATIONS

This application claims the benefit of U.S. Provisional Application Ser. No. 60/461,977 filed Apr. 10, 2003.

BACKGROUND OF THE INVENTION

Melatonin has been shown to exert its biological effects through binding to specific G-protein coupled receptors. Two melatonin receptors have been identified in humans, MT$_1$ (me11a) and MT$_2$ (me11b) (Reppert, S. M. et al. *Proc. Natl. Acad. Sci.* 1995 92, 8734–8738 and Reppert, S. M. et al. *Neuron* 1994 13, 1177–1185). Specific [$^{125}$I]-2-iodomelatonin binding within the hypothalamus is completely localized to the suprachiasmatic nucleus, strongly suggesting the melatonin receptors are located within the structures containing the human biological clock. Recent evidence has shown that it is the MT$_2$ receptor that is primarily involved in the regulation of circadian rhythms (Dubocovich, M. L. et al. *Adv. Exp. Med. Biol.* 1999 460, 181–190), and selective MT$_2$ receptor antagonists have demonstrated the ability to block melatonin-mediated phase advances of circadian rhythms (Dubocovich, M. L. et al. *FASEB J.* 1998 12, 1211–1219).

Thus, selective MT$_2$ receptor antagonists should be particularly useful for the treatment of sleep and chronobiotic disorders in which uncontrolled or undesirable effects of endogenously secreted melatonin would be advantageously blocked. Other indications affected by melatonin activity include depression, mood disorders, seasonal affective disorder, synchronization of biological rhythms in the blind, jet lag, work shift syndrome, immune disorders, premenstrual syndrome, reproductive disorders, neuroendocrine disorders, and resetting of the biological clock.

The novel tetrahydroisoquinoline compounds disclosed in this invention and the use of all of the tetrahydroisoquinoline compounds disclosed in this invention for treating disorders associated with abnormal melatonin conditions are not taught or suggested by the prior art.

Certain N-acyl-1-phenethyl-1,2,3,4-tetrahydroisoquinolines have been disclosed as alkaloid intermediates and cardiovascular agents. See the following references: Itoh, T. et al. *Tetrahedron* 2001 57, 8827–8839; Osante, I. et al. *European Journal of Organic Chemistry* 2001 7, 1267–1277; Venkov, A. P. and Lukanov, L. K. *Synth. Commun.* 1996 26, 755–62; Ishikawa, K. et al. U.S. Pat. No. 5,362,736, 1994; Ishikawa, K. et al. EP 501693 A1, 1996; Dugar, S. and Kogan, T. U.S. Pat. No. 5,124,337, 1992; Czarnocki, Z. et al. *J. Chem. Soc., Chem. Commun.* 1987 7, 493–4; Czarnocki, Z. et al. *Can. J. Chem.* 1987 65, 2356–61; Marino, J. P. and Schwartz, A. *Tetrahedron Lett.* 1979, 35, 3253–6; Kupchan, S. M. et al. *J. Org. Chem.* 1978 43, 4076–81; Kupchan, S. M. et al. *J. Org. Chem.* 1978 43, 4464–8; Kupchan, S. M. et al. *J. Chem. Soc., Chem. Commun.* 1977 23, 847–8; Kupchan, S. M. et al. *J. Org. Chem.* 1978 43, 2521–9; Kupchan, S. M. et al. *J. Org. Chem.* 1976 41, 4049–50; Kupchan, S. M. et al. *J. Org. Chem.* 1976 41, 4047–9; Leimgruber, W. and Wick, A. E. U.S. Pat. No. 3,922,285, 1975; Marino, J. P. and Samanen, J. M. *Tetrahedron Lett.* 1973 (46), 4553–6; and Leimgruber, W. and Wick, A. E. Ger. Patent 2214498, 1972.

SUMMARY OF THE INVENTION

The present invention encompasses a novel series of compounds of Formula I, including all stereoisomers and pharmaceutically acceptable salts and solvates, wherein Ar, R$^1$, R$^2$, R$^3$, R$^4$, R$^5$, and R$^6$ are defined below. The compounds bind to melatonin receptors and are useful in the treatment of disorders related to the melatonergic system including sleep disorders, chronobiotic disorders, shifts in circadian cycles, seasonal affective disorders, melancholia, stress, appetite regulation, benign prostatic hyperplasia, and related conditions.

DETAILED DESCRIPTION OF THE INVENTION

The invention comprises compounds of Formula I and their use as melatonergic agents in treating disorders related abnormal melatonergic conditions. The compounds, including all stereoisomers and pharmaceutically acceptable salts and solvates, have the following formula and meanings:

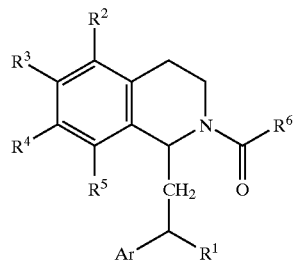

I wherein

Ar is phenyl optionally substituted with 1–3 substituents selected from the group consisting of halogen, C$_{1-6}$alkyl, and C$_{1-6}$alkoxy, or Ar is 2,3-dihydrobenzfuran-4-yl;

R$^1$ is C$_{1-6}$alkyl or phenyl wherein phenyl is optionally substituted with 1–3 substituents selected from the group consisting of halogen, C$_{1-6}$alkyl, and C$_{1-6}$alkoxy;

or Ar and R taken together with the carbon to which they are attached are 1-indanyl or 9-fluorenyl;

R$^2$, R$^3$, R$^4$, and R$^5$ are independently hydrogen, halo, C$_{1-3}$alkoxy, or C$_{1-6}$alkyl;

or R$^2$ and R$^3$ taken together, R$^3$ and R$^4$ taken together, or R$^4$ and R$^5$ taken together are —O(CH$_2$)$_{2-3}$— or —O(CH$_2$)$_{1-2}$O—;

R$^6$ is selected from the group consisting of hydrogen, C$_{1-9}$alkyl, C$_{3-7}$cycloalkyl, C$_{1-6}$alkoxy, C$_{1-2}$perfluoroalkyl, —CH$_2$OC$_{1-3}$alkyl, —(CH$_2$)$_{1-2}$CO$_2$R$^7$, —(CH$_2$)$_{1-2}$CO$_2$NR$^7_2$, —NR$^7_2$, —CH$_2$Cl, —CH$_2$OCOMe, —CH$_2$OPh, benzyl, 2-thienyl, 2-furanyl, 5-isoxazolyl, 4-biphenyl, naphthyl, 4-(1,2-methylenedioxy)phenyl, and phenyl where phenyl is optionally substituted with 1–3 substituents selected from halogen, C$_{1-3}$alkoxy, C$_{1-2}$perfluoroalkyl, C$_{1-2}$perfluoroalkoxy, and nitro; and R$^7$ is hydrogen or C$_{1-6}$alkyl;

or a stereoisomer, pharmaceutically acceptable salt, or solvate thereof.wherein

Ar is phenyl optionally substituted with 1–3 substituents selected from the group consisting of halogen, C$_{1-6}$alkyl, and C$_{1-6}$alkoxy, or Ar is 2,3-dihydrobenzfuran-4-yl;

R$^1$ is C$_{1-6}$alkyl or phenyl wherein phenyl is optionally substituted with 1–3 substituents selected from the group consisting of halogen, C$_{1-6}$alkyl, and C$_{1-6}$alkoxy;

or Ar and R taken together with the carbon to which they are attached are 1-indanyl or 9-fluorenyl;

R$^2$, R$^3$, R$^4$, and R$^5$ are independently hydrogen, halo, C$_{1-3}$alkoxy, or C$_{1-6}$alkyl;

or R$^2$ and R$^3$ taken together, R$^3$ and R$^4$ taken together, or R$^4$ and R$^5$ taken together are —O(CH$_2$)$_{2-3}$— or —O(CH$_2$)$_{1-2}$O—;

$R^6$ is selected from the group consisting of hydrogen, $C_{1-9}$alkyl, $C_{3-7}$cycloalkyl, $C_{1-6}$alkoxy, $C_{1-2}$perfluoroalkyl, —$CH_2OC_{1-3}$alkyl, —$(CH_2)_{1-2}CO_2R^7$, —$(CH_2)_{1-2}CO_2NR^7{}_2$, —$NR^7{}_2$, —$CH_2Cl$, —$CH_2OCOMe$, —$CH_2OPh$, benzyl, 2-thienyl, 2-furanyl, 5-isoxazolyl, 4-biphenyl, naphthyl, 4-(1,2-methylenedioxy)phenyl, and phenyl where phenyl is optionally substituted with 1–3 substituents selected from halogen, $C_{1-3}$alkoxy, $C_{1-2}$perfluoroalkyl, $C_{1-2}$perfluoroalkoxy, and nitro; and $R^7$ is hydrogen or $C_{1-6}$alkyl;

or a stereoisomer, pharmaceutically acceptable salt, or solvate thereof.

One aspect of the invention are compounds of Formula I where Ar and $R^1$ are each phenyl optionally substituted with 1–3 substituents selected from halogen, $C_{1-6}$alkyl, and $C_{1-6}$alkoxy.

Another aspect of the invention are compounds of Formula I where Ar is phenyl or 4-chlorophenyl and $R^1$ is phenyl.

Another aspect of the invention are compounds of Formula I where $R^4$ is $C_{1-3}$ alkoxy.

Another aspect of the invention are compounds of Formula I where selected from the group consisting of 1-(2,2-diphenyl-ethyl)-6,7-dimethoxy-3,4-dihydro-1H-isoquinoline-2-carbaldehyde;

1-[1-(2,2-diphenyl-ethyl)-6,7-dimethoxy-3,4-dihydro-1H-isoquinolin-2-yl]-ethanone;

1-[1-(2,2-diphenyl-ethyl)-6-bromo-7-methoxy-3,4-dihydro-1H-isoquinolin-2-yl]-ethanone;

1-[1-(2,2-diphenyl-ethyl)-6-bromo-7-methoxy-3,4-dihydro-1H-isoquinolin-2-yl]-heptanone;

1-[1-(2-(4-chlorophenyl)-2-phenyl-ethyl)-6,7-dimethoxy-3,4-dihydro-1H-isoquinolin-2-yl]-ethanone;

1-[1-(2,2-diphenyl-ethyl)-6,7-dimethoxy-3,4-dihydro-1H-isoquinolin-2-yl]-propan-1-one;

1-[1-(2,2-diphenyl-ethyl)-6,7-dimethoxy-3,4-dihydro-1H-isoquinolin-2-yl]-butan-1-one;

cyclopropyl-[1-(2,2-diphenyl-ethyl)-6,7-dimethoxy-3,4-dihydro-1H-isoquinolin-2-yl]-methanone;

1-[1-(2,2-diphenyl-ethyl)-6,7-dimethoxy-3,4-dihydro-1H-isoquinolin-2-yl]-phenyl-methanone;

1-[1-(2,2-diphenyl-ethyl)-6,7-dimethoxy-3,4-dihydro-1H-isoquinolin-2-yl]-2,2,2-trifluoro-ethanone;

1-(2,2-diphenyl-ethyl)-6,7-dimethoxy-3,4-dihydro-1H-isoquinoline-2-carboxylic acid amide;

1-(2,2-diphenyl-ethyl)-6,7-dimethoxy-3,4-dihydro-1H-isoquinoline-2-carboxylic acid methylamide;

1-(2,2-diphenyl-ethyl)-6,7-dimethoxy-3,4-dihydro-1H-isoquinoline-2-carboxylic acid methyl ester; and 1-[1-(2,2-diphenyl-ethyl)-7-methoxy-3,4-dihydro-1H-isoquinolin-2-yl]-ethanone.

Another aspect of the invention are compounds of Formula I where $R^3$ and $R^4$ taken together are —$O(CH_2)_{2-3}$— or —$O(CH_2)_{1-2}O$—.

Another aspect of the invention are methods of treating circadian-related disorders comprising the administration of a therapeutic amount of a compound of Formula Ia

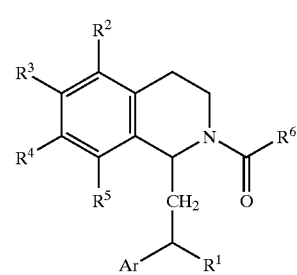

where:

Ar is phenyl optionally substituted with 1–3 substituents selected from the group consisting of halogen, $C_{1-6}$alkyl, and $C_{1-6}$alkoxy, or Ar is 2,3-dihydrobenzfuran-4-yl;

$R^1$ is hydrogen, $C_{1-6}$alkyl, or phenyl wherein phenyl is optionally substituted with 1–3 substituents selected from the group consisting of halogen, $C_{1-6}$alkyl, and $C_{1-6}$alkoxy;

or Ar and R taken together with the carbon to which they are attached are 1-indanyl or 9-fluorenyl;

$R^2$, $R^3$, $R^4$, and $R^5$ are independently hydrogen, halo, $C_{1-3}$alkoxy, or $C_{1-6}$alkyl;

or $R^2$ and $R^3$ taken together, $R^3$ and $R^4$ taken together, or $R^4$ and $R^5$ taken together are —$O(CH_2)_{2-3}$— or —$O(CH_2)_{1-2}O$—;

$R^6$ is selected from hydrogen, $C_{1-9}$alkyl, $C_{3-7}$cycloalkyl, $C_{1-6}$alkoxy, $C_{1-2}$perfluoroalkyl, —$CH_2OC_{1-3}$alkyl, —$(CH_2)_{1-2}CO_2R^7$, —$(CH_2)_{1-2}CO_2NR^7{}_2$, —$NR^7{}_2$, —$CH_2Cl$, —$CH_2OCOMe$, —$CH_2OPh$, benzyl, 2-thienyl, 2-furanyl, 5-isoxazolyl, 4-biphenyl, naphthyl, 4-(1,2-methylenedioxy)phenyl, and phenyl wherein phenyl is optionally substituted with 1–3 substituents selected from the group consisting of halogen, $C_{1-3}$alkoxy, $C_{1-2}$perfluoroalkyl, $C_{1-2}$perfluoroalkoxy, and nitro; and $R^7$ is hydrogen or $C_{1-6}$alkyl;

or a stereoisomer, pharmaceutically acceptable salt, or solvate thereof.

The invention includes all pharmaceutically acceptable salt forms of the compounds. Pharmaceutically acceptable salts are those in which the counter ions do not contribute significantly to the physiological activity or toxicity of the compounds and as such function as pharmacological equivalents. These salts can be made according to common organic techniques employing commercially available reagents. Some anionic salt forms include acetate, acistrate, besylate, bromide, chloride, citrate, fumarate, glucouronate, hydrobromide, hydrochloride, hydroiodide, iodide, lactate, maleate, mesylate, nitrate, pamoate, phosphate, succinate, sulfate, tartrate, tosylate, and xinofoate. Some cationic salt forms include ammonium, aluminum, benzathine, bismuth, calcium, choline, diethylamine, diethanolamine, lithium, magnesium, meglumine, 4-phenylcyclohexylamine, piperazine, potassium, sodium, tromethamine, and zinc.

The invention also includes all solvated forms of the compounds, particularly hydrates. Solvates do not contribute significantly to the physiological activity or toxicity of the compounds and as such function as pharmacological equivalents. Solvates may form in stoichiometric amounts or may form from adventitious solvent or a combination of both. One type of solvate is hydrate, and some hydrated forms include monohydrate, hemihydrate, and dihydrate.

The compounds of the invention may possess asymmetric carbon atoms, such as the structures shown below. The use of a single designation such as (R) or (S) is intended to include mostly one stereoisomer. Mixtures of stereoisomers can be separated into individual isomers according to common methods known in the art.

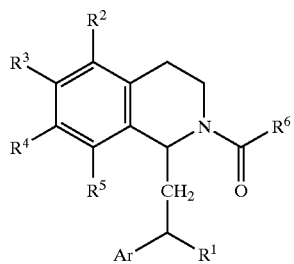

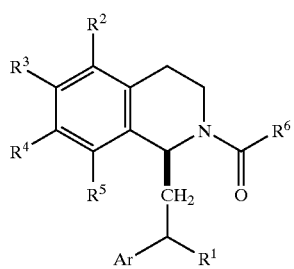

(S)

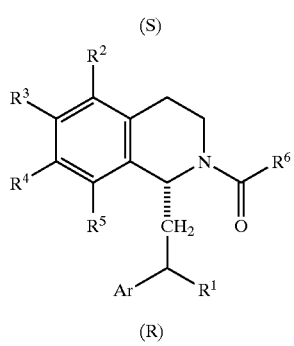

(R)

The invention includes all pharmaceutically acceptable salt forms of the compounds. Pharmaceutically acceptable salts are those in which the counter ions do not contribute significantly to the physiological activity or toxicity of the compounds and as such function as pharmacological equivalents. These salts can be made according to common organic techniques employing commercially available reagents. Some anionic salt forms include acetate, acistrate, besylate, bromide, chloride, citrate, fumarate, glucouronate, hydrobromide, hydrochloride, hydroiodide, iodide, lactate, maleate, mesylate, nitrate, pamoate, phosphate, succinate, sulfate, tartrate, tosylate, and xinofoate. Some cationic salt forms include ammonium, aluminum, benzathine, bismuth, calcium, choline, diethylamine, diethanolamine, lithium, magnesium, meglumine, 4-phenylcyclohexylamine, piperazine, potassium, sodium, tromethamine, and zinc.

The invention also includes all solvated forms of the compounds, particularly hydrates. Solvates do not contribute significantly to the physiological activity or toxicity of the compounds and as such function as pharmacological equivalents. Solvates may form in stoichiometric amounts or may form from adventitious solvent or a combination of both. One type of solvate is hydrate, and some hydrated forms include monohydrate, hemihydrate, and dihydrate.

Synthetic Methods

The compounds of the invention can be prepared by various procedures such as those illustrated in the reaction schemes and described in the examples. In all methods, the required starting materials are known or made using common organic reagents and reactions. One method for the construction of Formula I and Ia compounds is illustrated in Scheme 1. A formula IV amine can be reacted with a Formula III aldehyde in formic acid under conditions known collectively as the Pictet-Spengler reaction. The formula II compound produced can be acylated to form a Formula I or Ia compound.

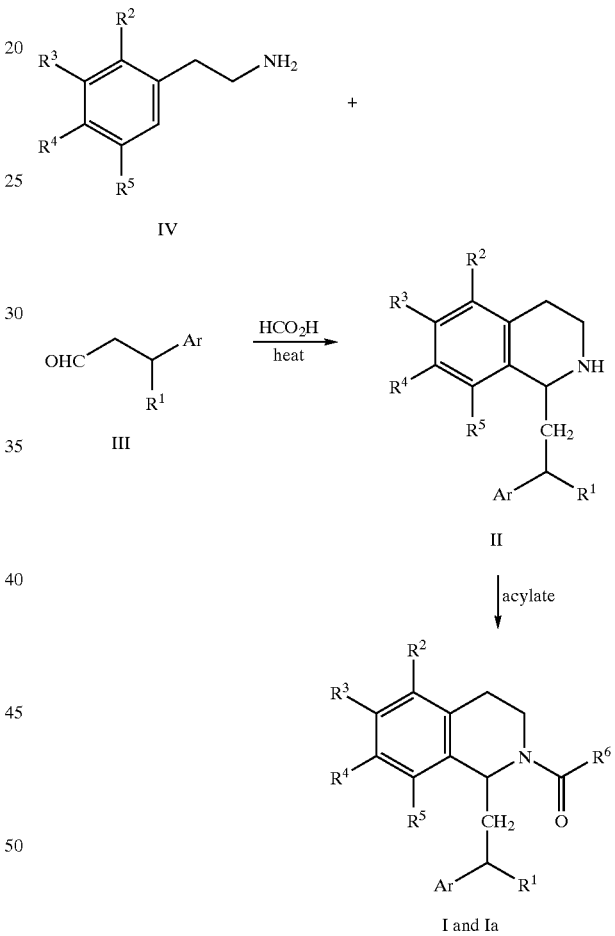

Another method for producing Formula I and Ia compounds, illustrated in Scheme 2, is to couple Formula IV amines with Formula V acids. The resulting amides (VI) can be cyclized using conventional condensing agents including phosphorous oxychloride in a Bischler-Napieralski reaction. The resulting Formula V compound can be reduced with a variety of reductants including sodium borohydride to form a Formula II compound. The Formula II compound may be acylated as described above to form a Formula I or Ia compound.

Scheme 2.

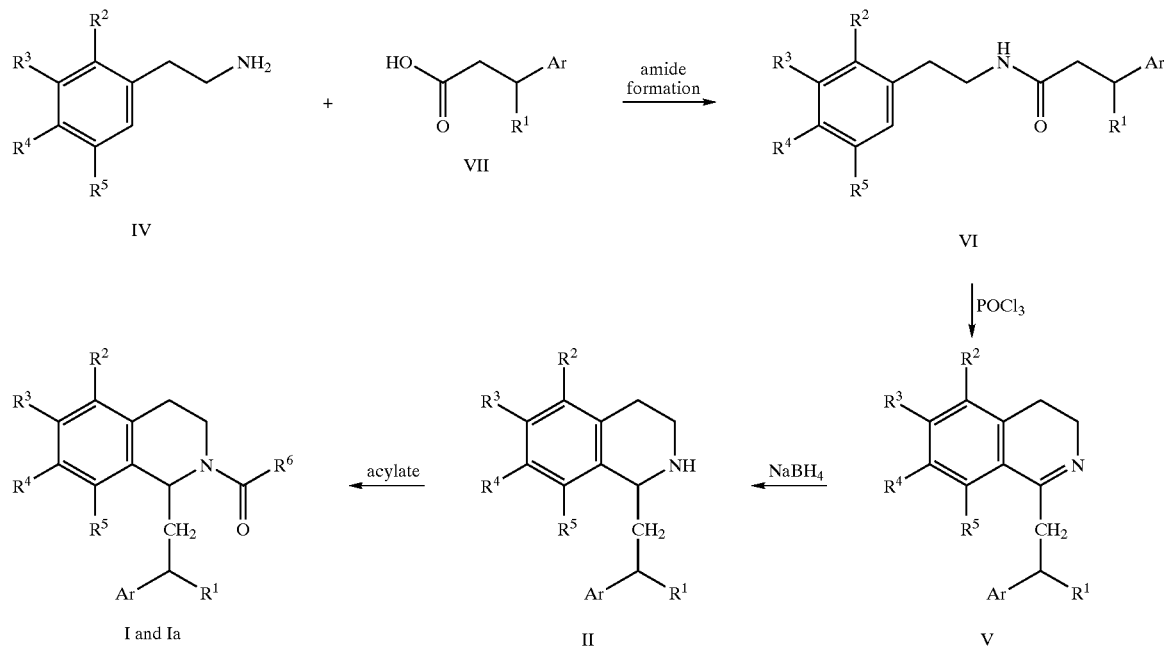

Biological Methods

Melatonin receptor binding assay. The compounds of this invention demonstrated melatonergic binding and functional antagonism as described in the following assays which are variations of assays known in the art (Reppert, S. M. et al. *Neuron* 1994 13, p. 1177–1185 and Reppert, S. M. et al. *Proc. Natl. Acad. Sci. USA* 1995 92, p. 8734–8738).

Reagents: (a) TME=50 mM Tris buffer containing 12.5 mM $MgCl_2$, and 2 mM EDTA, pH 7.4 at 37° C., with concentrated HCl; (b) wash buffer: 20 mM Tris base containing 2 mM $MgCl_2$, pH 7.4 at room temperature; (c) $10^{-4}$ M melatonin ($10^{-5}$ M final concentration); (d) 2-[$^{125}$I]-iodomelatonin $MT_1$, 0.1 nM final concentration; or (e) 2-[$^{125}$I]-iodomelatonin $MT_2$, 0.2 nM final concentration.

Membrane homogenates: melatonin $MT_1$ and $MT_2$ receptors cDNA were individually subcloned into pcDNA3 and introduced into NIH-3T3 cells using Lipofectamine. Transformed NIH-3T3 cells resistant to geneticin (G-418) were isolated, and single colonies expressing high levels of 2[$^{125}$I]-iodomelatonirn binding were isolated. Cells are maintained in DMEM supplemented with 10% calf serum and G-418 (0.5 g/liter). Cells are grown to confluency in T-175 flasks, scraped using Hank's balanced salt solution, and frozen at −80° C. For preparing membrane homogenates, pellets are thawed on ice, and re-suspended in TME buffer in the presence of 10 μg/ml aprotinin and leupeptin, and 100 μM phenylmethylsulfonylfluoride. The cells were then homogenized using a dounce homogenizer, and centrifuged. The resulting pellet was re-suspended with dounce homogenizer in TME (supplemented with the above protease inhibitors) and frozen. On the day of assay, a small aliquot was thawed on ice and re-suspended in the ice cold TME (1:50–1:100 v/v) and held on ice until assayed. Incubation is at 37° C. for 1 hour. Reaction is terminated by filtration. Filters were washed 3 times.

Melatonin induced cAMP accumulation in intact cells. Cells: the media was removed from cell flask and washed with Hank's salt solution or PBS, as appropriate. The cells were detached from flask. Enough media was added so that the concentration of cells is 4×105/ml when counted with a hemocytometer. Dialyzed or heat inactivated fetal bovine serum (FBS) was used in the media when plating the cells. 1 ml of cell suspension was put into each well, then 2 mls of media. Cells were incubated overnight. Stock solution: plain media (no serum or additives)+20 mM HEPES; IBMX solution: media/HEPES+1 mM IBMX; Assay solution: 90% stock solution+10% IBMX solution. Each well gets 3 mls of assay solution for preincubation and 3 mls for the assay. Each test condition is done in triplicate. Drug solutions: (a) basal assay solution+DMSO; (b) forskolin stimulation: 10 μM final concentration; (c) forskolin+competitor (melatonin): 10 μM final concentration forskolin plus desired concentration of competitor (melatonin).

All tests were done in triplicate at 37° C. Plates with cells were kept in a shallow 37° C. water bath throughout the reaction. Media was taken from the wells and 3 ml of preincubation media was added. After 10 min, that solution was removed and 3 mls of compound solution was added. After 10 min, the media was removed and reaction stopped with HCl. Samples set for at least an hour at room temperature. 1 ml from each dish was taken and put into a microfuge tube and spun to remove floating cells. After dilution to 1:100 for RIA, a radioimmunoassay was performed.

The compounds demonstrated binding to human $MT_1$ and $MT_2$ receptors (see Table 1). Binding data are reported as $IC_{50}$ values in the following ranges: +++=<100 nM, ++=100–1000 nM, +=>1000 nM. Examples 1–10 were evaluated for functional activity at the human $MT_2$ receptor and demonstrated full antagonism.

TABLE 1

| Example | MT$_2$ IC$_{50}$ (nM) |
| --- | --- |
| 1 | +++ |
| 2 | +++ |
| 3 | +++ |
| 4 | +++ |
| 5 | +++ |
| 6 | ++ |
| 7 | ++ |
| 8 | +++ |
| 9 | +++ |
| 10 | +++ |
| 11 | +++ |
| 12 | +++ |
| 13 | ++ |
| 14 | +++ |
| 15 | +++ |
| 16 | ++ |
| 17 | ++ |
| 18 | ++ |
| 19 | +++ |
| 20 | +++ |
| 21 | +++ |
| 22 | +++ |
| 23 | +++ |
| 24 | ++ |
| 25 | ++ |
| 26 | ++ |
| 27 | ++ |
| 28 | ++ |
| 29 | ++ |
| 30 | ++ |
| 31 | ++ |
| 32 | ++ |
| 33 | ++ |
| 34 | ++ |
| 35 | +++ |
| 36 | ++ |
| 37 | ++ |
| 38 | ++ |
| 39 | ++ |
| 40 | ++ |
| 41 | ++ |
| 42 | ++ |
| 43 | ++ |
| 44 | +++ |
| 45 | ++ |
| 54 | ++ |
| 55 | +++ |
| 56 | ++ |
| 57 | +++ |
| 58 | ++ |
| 59 | ++ |
| 60 | ++ |
| 61 | ++ |
| 62 | ++ |
| 63 | ++ |
| 64 | +++ |
| 65 | ++ |
| 66 | ++ |
| 67 | ++ |
| 68 | ++ |
| 69 | ++ |
| 70 | ++ |
| 78 | ++ |
| 79 | ++ |
| 80 | ++ |
| 81 | ++ |
| 82 | ++ |
| 83 | ++ |
| 84 | +++ |
| 85 | +++ |
| 86 | +++ |
| 87 | +++ |
| 88 | +++ |
| 89 | +++ |
| 90 | +++ |
| 91 | ++ |
| 92 | ++ |
| 93 | ++ |
| 94 | ++ |
| 95 | +++ |
| 96 | +++ |
| 97 | ++ |
| 98 | +++ |
| 99 | ++ |
| 100 | ++ |
| 101 | +++ |
| 102 | +++ |
| 103 | +++ |
| 104 | ++ |
| 105 | +++ |
| 106 | ++ |
| 107 | ++ |
| 108 | ++ |
| 109 | +++ |
| 110 | +++ |
| 111 | ++ |
| 112 | +++ |
| 113 | +++ |
| 114 | ++ |
| 115 | +++ |
| 116 | +++ |
| 117 | +++ |
| 118 | ++ |
| 119 | +++ |
| 120 | ++ |
| 121 | ++ |
| 122 | ++ |
| 123 | ++ |
| 124 | +++ |
| 125 | +++ |
| 126 | +++ |
| 127 | ++ |
| 128 | +++ |
| 129 | ++ |
| 130 | +++ |
| 131 | ++ |
| 132 | ++ |
| 133 | ++ |
| 134 | +++ |
| 135 | ++ |
| 136 | +++ |
| 137 | ++ |
| 138 | ++ |
| 139 | +++ |
| 140 | +++ |
| 141 | ++ |
| 142 | +++ |
| 143 | ++ |
| 144 | +++ |
| 145 | ++ |
| 146 | ++ |
| 147 | +++ |
| 148 | ++ |
| 149 | ++ |
| 150 | ++ |

Pharmaceutical Composition and Method of Treatment

The modulation of melatonin receptors contributes to the regulation of a variety of biological rhythms. Administration of melatonin itself has been shown to affect conditions including depression, jet-lag, work-shift syndrome, sleep disorders, glaucoma, some disorders associated with reproduction, cancer benign prostatic hyperplasia, immune disorders, and neuroendocrine disorders. Thus, selective MT$_2$ receptor antagonists should be particularly useful for the treatment of sleep and chronobiotic disorders in which the uncontrolled or undesirable effects of endogenously secreted melatonin would be advantageously blocked. Other indications affected by melatonin activity include depression, mood disorders, seasonal affective disorder, synchronization of biological rhythms in the blind, jet lag, work shift syndrome, immune disorders, premenstrual syndrome, reproductive disorders, neuroendocrine disorders, and resetting of the biological clock.

The invention also provides a method for treating a mammal, including man, afflicted with disorders associated with melatonergic receptors, especially circadian rhythm-related disorders, which comprises administering a therapeutically effective amount of a compound of Formula I or Ia or a nontoxic pharmaceutically acceptable salt, hydrate, or solvate thereof.

The term "therapeutically effective amount" means the total amount of each active component that is sufficient to show a meaningful patient benefit. That is, alleviating or ameliorating disorders associated with the melatonergic system. When applied to an individual active ingredient and administered alone, the term refers to that ingredient alone. When applied to a combination, the term refers to combined amounts of the active ingredients that result in the therapeutic effect, whether administered in combination, serially, or simultaneously. The terms "treat, treating, treatment" as used herein and in the claims have the meaning of alleviating or ameliorating stress, sleep disorders, seasonal depression, appetite regulation, shifts in circadian cycles, melancholia, benign prostate hyperplasia, inflammatory articular diseases, headaches and related conditions associated with melatonergic action.

For therapeutic use, the pharmacologically active compounds of Formula I and Ia will normally be administered as a pharmaceutical composition comprising the active ingredient in association with a solid or liquid pharmaceutically acceptable carrier, and optionally with pharmaceutically acceptable adjuvants and excipients employing standard conventional techniques.

The pharmaceutical compositions include suitable dosage forms for oral, parenteral (including subcutaneous, intramuscular, intradermal and intravenous) transdermal, bronchial or nasal administration. Thus, if a solid carrier is used, the preparation may be in the form of tablets, capsules, powders, pellets, lozenges, or other conventional forms. The solid carrier may contain conventional excipients such as binding agents, fillers, tableting lubricants, disintegrants, wetting agents and the like. If desired, the tablet may be film coated by conventional techniques. If a liquid carrier is employed, the preparation may be in the form of a syrup, emulsion, soft gelatin capsule, sterile vehicle for injection, an aqueous or non-aqueous liquid suspension, or may be a dry product for reconstitution with water or other suitable vehicle before use. Liquid preparations may contain conventional additives such as suspending agents, emulsifying agents, wetting agents, non-aqueous vehicle (including edible oils), preservatives, as well as flavoring and/or coloring agents.

For parenteral administration, a vehicle normally will comprise sterile water, at least in large part, although saline solutions, glucose solutions, and the like may be used. Conventional preservatives, buffering agents and the like also may be added to the parenteral dosage forms. Injectable suspensions also may be used, in which case conventional suspending agents may be employed.

Particularly useful is the administration of a compound of Formula I or Ia in oral dosage formulations. The pharmaceutical compositions are prepared by conventional techniques appropriate to the desired preparation containing appropriate amounts of the active ingredient. See for example, *Remington's Pharmaceutical Sciences*, Mack Publishing Company, Easton, Pa., 17th edition, 1985.

Some examples of suitable carriers and diluents include lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, water, syrup, methyl cellulose, methyl- and propyl-hydroxybenzoates, talc, magnesium stearate and mineral oil. The formulations can additionally include lubricating agents, wetting agents emulsifying and suspending agents, preserving agents, sweetening agents or flavoring agents. The compositions of the invention may be formulated so as to provide quick, sustained or delayed release of the active ingredient after administration to the patient.

The compositions are preferably formulated in a unit dosage form, each dosage containing from about 0.1 to 100 mg, more usually 1 to 10 mg, of the active ingredient. The term "unit dosage form" refers to physically discrete units suitable as unitary dosages for human subjects and other mammals, each unit containing a predetermined quantity of active material calculated to produce the desired therapeutic effect, in association with the required pharmaceutical carrier.

The dosage of the compounds of Formula I or Ia required to achieve a therapeutic effect will depend not only on such factors as the age, weight and sex of the patient, and mode of administration, but also on the degree of melatonergic activity desired and the potency of the particular compound being utilized for the particular disorder or condition concerned. It is also contemplated that the treatment and dosage of the particular compound may be administered in unit dosage form and that the unit dosage form would be adjusted accordingly by one skilled in the art to reflect the relative level of activity. The decision as to the particular dosage to be employed (and the number of times to be administered per day) is within the discretion of the physician, and may be varied by titration of the dosage to the particular circumstances of this invention to produce the desired therapeutic effect.

The compounds are effective over a wide dosage range. For example, dosages per day will normally fall within the range of about 0.1 to 500 mg. In the treatment of adult humans, the range of about 0.1 to 10 mg/day, in single or divided doses, is preferred. Generally, the compounds of the invention may be used in treating sleep and related disorders in a manner similar to that used for melatonin. However, it will be understood that the amount of the compound actually administered will be determined by a physician using sound medical judgement.

DESCRIPTION OF SPECIFIC EMBODIMENTS

Preparation of Formula VI Intermediates

Preparation 1

N-(2-p-methoxyphenylethyl)-p-fluorophenylpropionamide. To a stirred mixture of p-methoxyphenethyl amine (3.28 g, 21.7 mmol), p-fluorophenyl propionic acid (3.31 g, 19.7 mmol), and 150 ml anhydrous dichloromethane was added 1-[3-(dimethylamino)propyl]-3-ethylcarbodiimide hydrochloride (4.16 g, 21.7 mmol). The mixture was stirred at ambient temperature for 40 hours and then washed with 1N sodium hydroxide, 1N hydrochloric acid, and saturated sodium chloride, dried, filtered and evaporated to a green solid (5.41 g, 91%). 1H NMR (CDCl3) δ 7.18 (m, 2H); 6.98 (m, 4 H); 6.81 (d, 2 H); 5.32 (br s, 1 H); 3.79 (s, 3 H); 3.44 (q, 2 H); 2.90 (t, 2 H); 2.68 (t, 2 H); 2.39 (t, 2 H).

Preparation 2

N-(3,4-methylenedioxyphenylethyl)-p-fluorophenylpropionamide. A mixture of 3,4-methylenedioxyphenethyl amine (2.01 g, 9.92 mmol), p-fluorophenyl propionic acid (1.67 g, 9.92 mmol), and anhydrous dichloromethane was treated with 1-[3-(dimethylamino)propyl]-3-ethylcarbodiimide hydrochloride (2.09 g, 10.9 mmol) and stirred at ambient temperature for 60 hours. The mixture was diluted with dichloromethane, washed with 1N sodium hydroxide, 1N hydrochloric acid, saturated sodium chloride, dried and evaporated to a white solid. Silica gel chromatography (50% hexanes/ethyl acetate) afforded the product as a white solid (1.81 g, 58%). $^1$H NMR (CDCl$_3$) δ 7.14 (m, 2 H); 6.96 (t, 2 H); 6.66 (d, 1 H); 6.58 (s, 1 H); 6.53 (d, 1 H); 5.94 (s, 2 H); 5.35 (br s, 1 H); 3.43 (q, 2 H); 2.89 (t, 2 H); 2.63 (t, 2 H); 2.38 (t, 2 H).

Preparation 3

N-(2,3-dihydrobenzofuran-5-ethyl)-p-fluorophenylpropionamide. A mixture of 2,3-dihydrobenzofuran-5-ethylamine hydrochloride (0.36 g, 2.16 mmol) in dichloromethane (5 ml) was treated with triethylamine (0.33 ml, 2.37 mmol) followed by 1-[3-(dimethylamino)propyl]-3-ethylcarbodiimide hydrochloride (0.45 g, 2.35 mmol). The solution was stirred at ambient temperature for 12 hours and applied directly to a silica gel column. Elution with 50% hexanes/ethyl acetate afforded the product as a pale yellow solid (0.65 g, 96%). $^1$H NMR (CDCl$_3$) δ 7.14 (m, 2 H); 6.93 (m, 3 H), 6.71 (d, 1 H); 6.68 (d, 1 H); 5.35 (br s, 1 H); 4.55 (t, 2 H); 3.42 (t, 2 H); 3.17 (q, 2 H); 2.92 (t, 2 H); 2.66 (t, 2 H); 2.39 (t, 2 H).

Preparation of Formula V Intermediates

Preparation 4

1-(2-p-fluorophenylethyl)-7-methoxy-3,4-dihydroisoquinoline. N-(2-p-methoxyphenylethyl)-p-fluorophenylpropionamide (4.2 g, 13.9 mmol) was refluxed in phosphorous oxychloride (30 ml) for 3 hours and the solvent was removed by rotary evaporation. The residue was carefully basified with 5N sodium hydroxide and extracted into ethyl acetate. The pooled organic extracts were washed with saturated sodium chloride, dried and evaporated to a brown oil that solidified upon standing (2.10 g, 53%). $^1$H NMR (CDCl$_3$) δ 7.25 (m, 5 H); 6.91 (t, 2 H); 3.87 (s, 3 H); 3.80 (m, 2 H); 3.61 (t, 2 H); 3.14 (t, 2 H); 2.89 (t, 2 H). HPLC-MS (C-18, methanol/water/TFA linear gradient elution, 5 ml/min, 220 nm) single peak at 1.16 min; MS (ES+) obsd m/z=284.17.

Preparation 5

1-(2-p-fluorophenylethyl)-6,7-methylenedioxy-3,4-dihydroisoquinoline. N-(3,4-methylenedioxyphenylethyl)-p-fluorophenylpropionamide (0.90 g, 2.86 mmol) was stirred in refluxing phosphorous oxychloride (20 ml) for 6 hours and the solvent removed by rotary evaporation. The residue was carefully basified with 5N sodium hydroxide and extracted into ethyl acetate. The pooled organic extracts were washed with saturated sodium chloride, dried and evaporated to a yellow solid (0.79 g, 94%). $^1$H NMR (CDCl$_3$) δ 7.21 (m, 2 H); 6.98 (m, 3 H); 6.71 (s, 1 H); 6.02 (s, 2 H); 3.65 (t, 2 H); 3.02 (m, 4 H); 2.61 (t, 2 H).

Preparation 6

1-(2-p-fluorophenylethyl)-6,7-dihydrofuranyl-3,4-dihydroisoquinoline. N-(2,3-dihydrobenzofuran-5-ethyl)-p-fluorophenylpropionamide (0.65 g, 2.08 mmol) was refluxed in phosphorous oxychloride for 2 hours and the solvent removed by rotary evaporation. The residue was carefully basified with 5N sodium hydroxide and extracted into ethyl acetate. The pooled organic extracts were washed with saturated sodium chloride, dried, and evaporated to a yellow oil that solidified upon standing (0.49 g, 80%). $^1$H NMR (CDCl$_3$) δ 7.19 (m, 2 H); 6.98 (m, 4 H); 4.58 (t, 2 H); 3.62 (t, 2 H); 3.22 (t, 2 H); 2.94 (br s, 4 H); 2.58 (t, 2 H).

Preparation of Formula II Intermediates

Preparation 7

1-(2,2-diphenyleth-1-yl)-6,7-dimethoxy-1,2,3,4-tetrahydroisoquinoline. A solution of 3,3-diphenylpropionaldehyde (19.25 g, 91.54 mmoles) and 2-(3,4-dimethoxyphenyl)ethylamine (16.59 g, 1 equiv.) in 90% formic acid 125 mL) was heated at 95° C. for 16 hours. Upon cooling to room temperature, the solvent was removed on the rotary evaporator, and the residue was partitioned between ethyl acetate and 1M sodium hydroxide. The organic phase was washed with 1M sodium hydroxide and brine, dried over sodium sulfate, and evaporated to give a thick gum. The product was purified by flash chromatography on silica gel, eluting with 20:1 ethyl acetate/methanol, to give a thick gum that solidified upon standing (17.01 g, 50%). $^1$H-NMR (CDCl$_3$) δ 2.42 (m, 1H), 2.53 (m, 1H), 2.67 (m, 2H), 2.98 (m, 1H), 3.18 (m, 1H), 3.77 (ABq, 1H), 3.84 and 3.88 (s, each 3H), 4.48 (ABq, 1H), 6.46 and 6.57 (s, each 1H), 7.32 (m, 10 H). Mass spec. 374.2 (MH)$^+$.

Preparation 8

1-(2-p-fluorophenylethyl)-7-methoxy-1,2,3,4-tetrahydroisoquinoline. A solution of 1-(2-p-fluorophenylethyl)-7-methoxy-3,4-dihydroisoquinoline (1.04 g, 3.67 mmol) in methanol (7 ml) was treated with sodium borohydride (0.56 g, 14.7 mmol) and heated at reflux for one hour. The mixture was cooled and evaporated. The residue was mixed with 1N sodium hydroxide and ethyl acetate and extracted into ethyl acetate. The pooled extracts were washed with saturated sodium chloride, dried, and evaporated to a brown oil (0.59 g, 57%). HPLC-MS (C-18, methanol/water/TFA linear gradient elution, 5 ml/min, 220 nm) single peak at 1.12 min; MS (ES+) obsd m/z=286.34.

Preparation 9

1-(2-p-fluorophenylethyl)-6,7-methylenedioxy-1,2,3,4-tetrahydroisoquinoline. A solution of 1-(2-p-fluorophenylethyl)-6,7-methylenedioxy-3,4-dihydroisoquinoline (0.78 g, 2.67 mmol) in methanol (7 ml) was treated with sodium borohydride (0.30 g, 8.01 mmol) and heated at reflux for two hours. The mixture was cooled and evaporated. The residue was mixed with 1N sodium hydroxide and ethyl acetate and extracted into ethyl acetate. The pooled extracts were washed with saturated sodium chloride, dried, and evaporated to a pale yellow oil (0.56 g, 70%). $^1$H NMR (CDCl$_3$) δ 7.18 (m, 2 H); 6.97 (m, 2 H); 6.58 (m, 2 H), 5.88 (s, 2 H); 3.90 (m, 1 H); 3.21 (m, 1 H); 2.99 (m, 1 H); 2.81–2.62 (m, 4 H); 2.06 (m, 2 H). HPLC-MS (C-18, methanol/water/TFA linear gradient elution, 5 ml/min, 220 nm) single peak at 1.13 min; MS (ES+) obsd m/z=299.87.

Preparation 10

1-(2-p-fluorophenylethyl)-6,7-dihydrofuranyl-1,2,3,4-tetrahydroisoquinoline. A solution of 1-(2-p-fluorophenylethyl)-6,7-dihydrofuranyl-3,4-dihydroisoquinoline (0.49 g, 1.66 mmol) in methanol (6 ml) was treated with sodium borohydride (0.25 g, 6.69 mmol) and heated at reflux for two hours. The mixture was cooled and evaporated. The residue was mixed with 1N sodium hydroxide and ethyl acetate and extracted into ethyl acetate. The pooled extracts were washed with saturated sodium chloride, dried, and evaporated to a waxy solid (0.44 g, 88%). HPLC-MS (C-18, methanol/water/TFA linear gradient elution, 5 ml/min, 220 nm) single peak at 1.26 min; MS (ES+) obsd m/z =297.88.

Synthesis of Formula I Compounds

EXAMPLE 1

N-acetyl 1-(2,2-diphenyleth-1-yl)-6,7-dimethoxy-1,2,3,4-tetrahydroisoquinoline. A stirred solution of 1-(2,2-diphenyleth-1-yl)-6,7-dimethoxy-1,2,3,4-tetrahydroisoquinoline (1.8942 g, 5.0720 mmoles) in methylene chloride (15 mL) at 0° C. was treated with triethylamine (0.707 mL, 1.5 equiv.) and acetic anhydride (0.844 mL, 1.5 equiv.). After 2 hours at room temperature, The mixture was diluted with ether and washed with 1M sodium hydroxide (2×), water, and brine. The organic phase was dried over sodium sulfate and evaporated to give the product as a colorless foam (2.0178 g, 96%). $^1$H-NMR (CDCl$_3$) δ (approx. 1.8:1 ratio of rotomers) 1.65 (rotomer A, s, 3H), 1.96 (rotomer B, s, 3H), 2.35 (rotomer B, m, 1H), 2.54 (rotomer A, m, 1H), 2.67 (rotomer A, m, 1H), 2.80 (rotomers A & B, m, 1H), 2.94 (rotomer A, m, 1H), 3.21 (rotomer A, m, 1H), 3.43 (rotomers A & B, m, 1H), 3.77 (rotomer B, s, 3H), 3.88 (rotomers A & B, s, 3H), 3.92 (rotomer A, s, 3H), 4.03 (rotomer A, m, 1H), 4.12 (rotomer B, t, 1H), 4.60 (rotomer B, m, 1H), 5.68 (rotomer A, m, 1H), 6.38 (rotomer B, s, 1H), 6.53 (rotomer A, s, 1H), 6.60 (rotomer B, s, 1H), 6.62 (rotomer A, s, 1H), 7.32 (rotomers A & B, m, 10H). Mass spec. 416.4 (MH)$^+$. Anal. Calc. for C$_{27}$H$_{29}$NO$_3$-2/3H$_2$O: C-75.85, H-7.15, N-3.28. Found: C-75.89, H-7.03, N-3.24.

EXAMPLE 2

N-formyl 1-(2,2-diphenyleth-1-yl)-6,7-dimethoxy-1,2,3,4-tetrahydroisoquinoline. A solution of 1-(2,2-diphenyleth-1-yl)-6,7-dimethoxy-1,2,3,4-tetrahydroisoquinoline (1.0090 g, 2.7015 mmoles) and p-nitrophenyl formate (474.0 mg, 1.05 equiv.) in methylene chloride (10 mL) was stirred at room temperature for 16 hours. The mixture was diluted with ether and washed with 1M sodium hydroxide (2×), water, and brine. The organic phase was dried over sodium sulfate and evaporated to give the product as a colorless solid foam (1.0629 g, 98%). $^1$H-NMR (CDCl$_3$) δ (approx. 1.8:1 mixture of rotomers) 2.45–3.20 (rotomers A & B, m, 4H), 3.48 (rotomer A, m, 1H), 3.74 (rotomer B, s, 3H), 3.83 (rotomer B, s, 3H), 3.86 (rotomer A, s, 3H), 3.89 (rotomer A, s, 3H), 4.01 (rotomer A, ABq, 1H), 4.16 (rotomer B, t, 1H), 4.22 (rotomer A, ABq, 1H), 4.52 (rotomer A, ABq, 1H), 5.40 (rotomer B, ABq, 1H), 6.30 (rotomer B, s, 1H), 6.47 (rotomer A, s, 1H), 6.55 (rotomer B, s, 1H), 6.61 (rotomer A, s, 1H), 7.30 (rotomers A & B, m, 10H), 7.89 (rotomer A, s, 1H), 8.09 (rotomer B, s, 1H). Mass spec. 402.4 (MH)$^+$. Anal. Calc. for C$_{26}$H$_{27}$NO$_3$: C-77.78, H-6.78, N-3.49. Found: C-77.74, H-6.93, N-3.30.

EXAMPLE 3

N-propionyl 1-(2,2-diphenyleth-1-yl)-6,7-dimethoxy-1,2,3,4-tetrahydroisoquinoline. This was prepared as described for example 1 above (596.1 mg, 98%). $^1$H-NMR (CDCl$_3$) δ (approx. 2:1 ratio of rotomers) 0.91 (rotomer A, t, 3H), 1.14 (rotomer B, t, 3H), 1.80 (rotomer A, m, 1H), 2.17 (rotomer B, m, 2H), 2.33 (rotomer A, m, 2H), 2.45–3.20 (rotomers A & B, m, 4H), 3.44 (rotomer B, m, 2H), 3.71 (rotomer B, s, 3H), 3.87 (rotomers A & B, s, 3H), 3.90 (rotomer A, s, 3H), 4.01 (rotomer A, ABq, 1H), 4.10 (rotomer B, t, 1H), 4.64 (rotomer A, m, 1H), 5.69 (rotomer B, t, 1H), 6.30 (rotomer B, s, 1H), 6.52 (rotomer A, s, 1H), 6.60 (rotomers A & B, s, 1H), 7.34 (rotomers A & B, m, 10H). Mass spec. 430.3 (MH)$^+$. Anal. Calc. for C$_{28}$H$_{31}$NO$_3$: C-78.29, H-7.27, N-3.26. Found: C-78.12, H-7.23, N-3.15.

EXAMPLE 4

N-butyryl 1-(2,2-diphenyleth-1-yl)-6,7-dimethoxy-1,2,3,4-tetrahydroisoquinoline. This was prepared as described for example 1 above (664.9 mg, 99%). $^1$H-NMR (CDCl$_3$) δ (approx. 2:1 ratio of rotomers) 0.87 (rotomer A, t, 3H), 1.05 (rotomer B, t, 3H), 1.18 (rotomers A & B, m, 2H), 1.78 (rotomer A, m, 1H), 2.15 (rotomer B, m, 2H), 2.31 (rotomer A, m, 2H), 2.45–3.20 (rotomers A & B, m, 4H), 3.43 (rotomer B, m, 2H), 3.68 (rotomer B, s, 3H), 3.85 (rotomers A & B, s, 3H), 3.90 (rotomer A, s, 3H), 4.00 (rotomer A, ABq, 1H), 4.15 (rotomer B, t, 1H), 4.66 (rotomer A, m, 1H), 5.67 (rotomer B, t, 1H), 6.30 (rotomer B, s, 1H), 6.51 (rotomer A, s, 1H), 6.58 (rotomers A & B, s, 1H), 7.32 (rotomers A & B, m, 10H). Mass spec. 444.3 (MH)$^+$. Anal. Calc. for C$_{29}$H$_{33}$NO$_3$-1/3H$_2$O: C-77.47, H-7.55, N-3.12. Found: C-77.38, H-7.50, N-3.19.

EXAMPLE 5

N-cyclopropylcarbonyl 1-(2,2-diphenyleth-1-yl)-6,7-dimethoxy-1,2,3,4-tetrahydroisoquinoline. This was prepared as described for example 1 above (515.8 mg, 100%). $^1$H-NMR (CDCl$_3$) δ (approx. 1.8:1 ratio of rotomers) 0.40 (rotomer A, m, 4H), 0.42 (rotomer B, m, 4H), 1.21 (rotomers A & B, m, 1H), 2.45–3.20 (rotomers A & B, m, 4H), 3.46 (rotomer B, m, 2H), 3.70 (rotomer B, s, 3H), 3.88 (rotomers A & B, s, 3H), 3.91 (rotomer A, s, 3H), 4.05 (rotomer A, ABq, 1H), 4.16 (rotomer B, t, 1H), 4.66 (rotomer A, m, 1H), 5.66 (rotomer B, t, 1H), 6.27 (rotomer B, s, 1H), 6.53 (rotomer A, s, 1H), 6.61 (rotomers A & B, s, 1H), 7.32 (rotomers A & B, m, 10H). Mass spec. 442.3. (MH)$^+$. Anal. Calc. for C$_{29}$H$_{31}$NO$_3$-2/3H$_2$O: C-76.80, H-7.18, N-3.09. Found: 76.97, H-7.10, N-3.08.

EXAMPLE 6

N-benzoyl 1-(2,2-diphenyleth-1-yl)-6,7-dimethoxy-1,2,3,4-tetrahydroisoquinoline. This was prepared as described for example 1 above (288.9 mg, 98%). $^1$H-NMR (CDCl$_3$) δ (approx. 2.4:1 ratio of rotomers) 2.40–3.20 (rotomers A & B, m, 4H), 3.47 (rotomer A, m, 2H), 1.62 (rotomer B, m, 2H), 3.71 (rotomer B, s, 3H), 3.77 (rotomer A, s, 3H), 3.86 (rotomer A, s, 3H), 3.89 (rotomer B, s, 3H), 4.29 (rotomer A, t, 1H), 4.68 (rotomer B, m, 1H), 4.80 (rotomer B, t, 1H), 5.76 (rotomer A, m, 1H), 6.01 (rotomer B, s, 1H), 6.35 (rotomer A, s, 1H), 6.52 (rotomer A, s, 1H), 6.67 (rotomer B, s, 1H), 6.85–7.65 (rotomers A & B, m, 15H). Mass spec. 478.5 (MH)$^+$. Anal. Calc. for C$_{32}$H$_{31}$NO$_3$-1/3H$_2$O: C-79.48, H-6.53, N-2.89. Found: C-79.49, H-6.41, N-2.70.

EXAMPLE 7

N-trifluoroacetyl 1-(2,2-diphenyleth-1-yl)-6,7-dimethoxy-1,2,3,4-tetrahydroisoquinoline. This was prepared as described for example 1 above (529.1 mg, 98%).

¹H-NMR (CDCl₃) δ 2.45 (m, 1H), 2.83 (m, 3H), 3.62 (m, 1H), 3.77 (s, 3H), 3.83 (s, 3H), 4.07 (t, 1H), 5.50 (ABq, 1H), 6.29 (s, 1H), 6.59 (s, 1H), 7.30 (m, 10H). Mass spec. 470.5 (MH)⁺. Anal. Calc. for $C_{27}H_{26}NO_3F_3$: C-69.07, H-5.58, N-2.98. Found: C-68.90, H-5.58, N-2.91.

EXAMPLE 8

N-carbamoyl 1-(2,2-diphenyleth-1-yl)-6,7-dimethoxy-1,2,3,4-tetrahydroisoquinoline. A solution of 1-(2,2-diphenyleth-1-yl)-6,7-dimethoxy-1,2,3,4-tetrahydroisoquinoline (1.0598 g, 2.838 mmoles) and urea (1.704 g, 10 equiv.) was heated at reflux. After 3 hours, TLC indicated less than 15% conversion. More urea (15.5 g, 90 equiv.) was added. Reflux continued for 24 hours. The solvent was then evaporated and the residue dissolved in water (80 mL). A white solid formed. After 1 hour, the solid was collected by filtration, washed with water, and dried in vacuo overnight (1.0554 g, 89%). ¹H-NMR (CDCl₃) δ 2.49 (m, 1H), 2.69 (m, 2H), 2.90 (m, 1H), 3.37 (m, 1H), 3.82 (s, 3H), 3.86 (s, 3H), 3.89 (m, 2H), 4.05 (t, 1H), 4.38 (m, 1H), 6.41 (s, 1H), 6.60 (s, 1H), 7.29 (m, 10H). Mass spec. 417.3 (MH)⁺. Anal. Calc. for $C_{26}H_{28}N_2O_3$: C-74.98, H-6.78, N-6.73. Found: C-74.72, H-6.74, N-6.45.

EXAMPLE 9

N-methylcarbamoyl 1-(2,2-diphenyleth-1-yl)-6,7-dimethoxy-1,2,3,4-tetrahydroisoquinoline. A stirred solution of 1-(2,2-diphenyleth-1-yl)-6,7-dimethoxy-1,2,3,4-tetrahydroisoquinoline (487.6 mg, 1.306 mmoles) in methylene chloride (5 mL) at 0° C. was treated with triethylamine (0.24 mL, 1.3 equiv.) and methyl isocyanate (0.10 mL, 1.3 equiv.). The mixture was immediately allowed to warm to room temperature. After 4 hours, the mixture was evaporated and the residue partitioned between ether and 2% phosphoric acid. The organic phase was washed with 1M sodium hydroxide and brine, dried over sodium sulfate, and evaporated to give a solid foam that was triturated with hexane to give the product as a white solid (494.8 mg, 88%).

¹H-NMR (CDCl₃) δ 2.45 (m, 1H), 2.65–3.10 (m, 3H), 2.73 (s, 3H), 3.38 (m, 1H), 3.79 (s, 3H), 3.85 (s, 3H), 3.90 (m, 2H), 4.03 (t, 1H), 4.45 (m, 1H), 6.38 (s, 1H), 6.58 (s, 1H), 7.32 (m, 10H). Mass spec. 431.2 (MH)⁺. Anal. Calc. for $C_{27}H_{30}N_2O_3$: C-75.32, H-7.02, N-6.51. Found: C-75.04, H-7.13, N-6.35.

EXAMPLE 10

N-carbomethoxy 1-(2,2-diphenyleth-1-yl)-6,7-dimethoxy-1,2,3,4-tetrahydroisoquinoline. This was prepared as described for the example above, replacing methyl chloroformate for methyl isocyanate (442.2 mg, 99%). ¹H-NMR (CDCl₃) δ 2.53 (m, 1H), 2.70–3.15 (m, 3H), 3.45 (m, 1H), 3.77 (s, 3H), 3.83 (s, 3H), 3.86 (s, 3H), 3.93 (m, 2H), 4.15 (t, 1H), 4.67 (m, 1H), 6.43 (s, 1H), 6.61 (s, 1H), 7.35 (m, 10H). Mass spec. 432.2 (MH)⁺. Anal. Calc. for $C_{27}H_{29}NO_4 \cdot 1/3H_2O$: C-74.12, H-6.83, N-3.20. Found: C-74.12, H-6.79, N-3.24.

EXAMPLES 11–150

Combinatorial Method of Synthesis of Formula I Compounds

N-acylated derivatives were prepared in parallel combinatorial fashion in 48 tube reactor vessels. For each derivative, a 0.46M solution of the tetrahydroisoquinoline (100 μl, 46 μmole) in 1,2-dichloroethane was treated with 0.077M acid chloride or chloroformate (900 μl, 69 μmole) and poly(4-vinylpyridine), 2% cross-linked (50 mg). The reactor was shaken at 550 rpm at ambient temperature for 18 hours. Wa21J (Supelco) polyamine scavenging resin (100 mg) was added and shaking continued 4 hours. The reaction mixtures were filtered into custom microtubes and concentrated by centrifugal evaporation. All products were analyzed by HPLC (C-18, methanol/water/TFA linear gradient elution, 5 ml/min, 220 nm) and positive ion mass spectrometry. Table 2 tabulates analytical data for examples 11–150.

TABLE 2

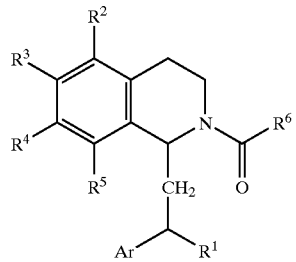

| Example | Ar | R¹ | R² | R³ | R⁴ | R⁵ | R⁶ | LC RT (min) | AP | MS (ES+) (M + H) |
|---|---|---|---|---|---|---|---|---|---|---|
| 1 | Ph | Ph | H | OMe | OMe | H | Me | | | |
| 2 | Ph | Ph | H | OMe | OMe | H | H | | | |
| 3 | Ph | Ph | H | OMe | OMe | H | Et | | | |
| 4 | Ph | Ph | H | OMe | OMe | H | Pr | | | |
| 5 | Ph | Ph | H | OMe | OMe | H | cPr | | | |
| 6 | Ph | Ph | H | OMe | OMe | H | Ph | | | |
| 7 | Ph | Ph | H | OMe | OMe | H | CF₃ | | | |
| 8 | Ph | Ph | H | OMe | OMe | H | NH₂ | | | |
| 9 | Ph | Ph | H | OMe | OMe | H | NHMe | | | |
| 10 | Ph | Ph | H | OMe | OMe | H | OMe | | | |
| 11 | Ph | Ph | H | OMe | OMe | H | SO₂(4-NO₂)Ph | na | 79 | 458.18 |
| 12 | Ph | Ph | H | OMe | OMe | H | SO₂Me | na | 87 | 452.32 |
| 13 | Ph | Ph | H | OMe | OMe | H | 2-thienyl | na | 97 | 484.12 |

TABLE 2-continued

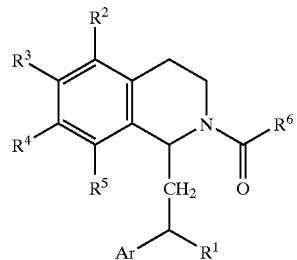

| Example | Ar | R¹ | R² | R³ | R⁴ | R⁵ | R⁶ | LC RT (min) | AP | MS (ES+) (M + H) |
|---|---|---|---|---|---|---|---|---|---|---|
| 14 | Ph | H | H | OMe | OMe | H | Me | 3.11 | 85 | 340.26 |
| 15 | Ph | H | H | OMe | OMe | H | H | na | 99 | 326.06 |
| 16 | Ph | H | H | OMe | OMe | H | NH₂ | na | 99 | 341.13 |
| 17 | Ph | Ph | H | OMe | H | H | Me | na | 99 | 386.31 |
| 18 | Ph | Me | H | OMe | OMe | H | Me | na | 95 | 354.47 |
| 19 | Ph | Ph | H | H | OMe | H | Me | 3.57 | 90 | 386.24 |
| 20 | Ph | Ph | H | H | OMe | H | Me | na | 99 | 386.51 |
| 21 | Ph | Ph | H | OMe | H | OMe | Me | na | 97 | 416.54 |
| 22 | Ph | Ph | H | Br | OMe | H | Me | 3.70 | 90 | 464.18 |
| 23 | Ph | Ph | H | Br | OMe | H | Me | na | 98 | 465.41 |
| 24 | Ph | Ph | OMe | OMe | H | H | Me | na | 98 | 416.54 |
| 25 | 4-MeOPh | 4-MeOPh | H | OMe | OMe | H | Me | na | 98 | 476.59 |
| 26 | 9-Fluoreneyl | | H | OMe | OMe | H | Me | na | 96 | 414.52 |
| 27 | Ph | Ph | CH₂CH₂O | H | H | H | Me | 4.39 | 91 | 398 |
| 28 | Ph | Ph | H | F | H | H | Me | 4.41 | 95 | 374 |
| 29 | Ph | Ph | OMe | H | H | H | Me | na | 97 | 386.51 |
| 30 | Ph | Ph | H | Br | OMe | H | 2-furanyl | 3.83 | 80 | 516.193 |
| 31 | Ph | Ph | H | Br | OMe | H | CH₂OPh | 3.91 | 70 | 556.2 |
| 32 | Ph | Ph | H | Br | OMe | H | cBu | 3.93 | 80 | 504.22 |
| 33 | Ph | Ph | H | Br | OMe | H | cHex | 4.07 | 80 | 532.26 |
| 34 | Ph | Ph | H | Br | OMe | H | Pentyl | 4.1 | 85 | 520.27 |
| 35 | Ph | Ph | H | Br | OMe | H | Hexyl | 4.25 | 95 | 534.28 |
| 36 | Ph | Ph | H | Br | OMe | H | neopentyl | 4.02 | 80 | 520.29 |
| 37 | Ph | Ph | H | Br | OMe | H | 3-NO₂Ph | 3.83 | 81 | 571.21 |
| 38 | Ph | Ph | H | Br | OMe | H | 4-NO₂Ph | 3.82 | 70 | 571.2 |
| 39 | Ph | Ph | H | Br | OMe | H | 4-MePh | 3.99 | 70 | 540.24 |
| 40 | Ph | Ph | H | Br | OMe | H | 4-CF₃Ph | 3.96 | 75 | 59423 |
| 41 | Ph | Ph | H | OMe | OMe | H | 2-furanyl | 3.53 | 70 | 468.27 |
| 42 | Ph | Ph | H | OMe | OMe | H | 2-MeOPh | 3.59 | 84.4 | 508.34 |
| 43 | Ph | Ph | H | OMe | OMe | H | cBu | 3.64 | 85 | 456.32 |
| 44 | Ph | Ph | H | OMe | OMe | H | cHex | 3.76 | 85 | 484.37 |
| 45 | Ph | Ph | H | OMe | OMe | H | Hexyl | 3.88 | 100 | 486.37 |
| 46 | Ph | Ph | H | OMe | OMe | H | Nonyl | 4.31 | 92 | 528.45 |
| 47 | Ph | Ph | H | OMe | OMe | H | neopentyl | 3.72 | 85 | 472.34 |
| 48 | Ph | Ph | H | OMe | OMe | H | 4-MeOPh | 3.6 | 75 | 508.35 |
| 49 | Ph | Ph | H | OMe | OMe | H | 3-NO₂Ph | 3.57 | 75 | 523.33 |
| 50 | Ph | Ph | H | OMe | OMe | H | 4-NO₂Ph | 3.57 | 95 | 523.32 |
| 51 | Ph | Ph | H | OMe | OMe | H | 4-MePh | 3.60 | 80 | 492.34 |
| 52 | Ph | Ph | H | OMe | OMe | H | CH₂Ph | 3.62 | 80 | 492.33 |
| 53 | Ph | Ph | H | OMe | OMe | H | 3,5-(CF₃)₂Ph | 3.88 | 75 | 614.34 |
| 54 | Ph | Ph | H | OMe | OMe | H | 4-CF₃Ph | 3.72 | 73 | 546.32 |
| 55 | Ph | H | H | OMe | OMe | H | 2-furanyl | 3.32 | 82 | 392.23 |
| 56 | Ph | H | H | OMe | OMe | H | CH₂Oph | 3.44 | 75 | 432.29 |
| 57 | Ph | H | H | OMe | OMe | H | cBu | 3.42 | 80 | 380.25 |
| 58 | Ph | H | H | OMe | OMe | H | cHex | 3.61 | 85.2 | 408.31 |
| 59 | Ph | H | H | OMe | OMe | H | iPr | 3.47 | 80 | 368.24 |
| 60 | Ph | H | H | OMe | OMe | H | pentyl | 3.61 | 85 | 396.3 |
| 61 | Ph | H | H | OMe | OMe | H | hexyl | 3.72 | 95 | 410.35 |
| 62 | Ph | H | H | OMe | OMe | H | nonyl | 4.1 | 95 | 452.38 |
| 63 | Ph | H | H | OMe | OMe | H | neopentyl | 3.56 | 88 | 396.3 |
| 64 | Ph | H | H | OMe | OMe | H | 4-MeOPh | 3.44 | 70 | 432.29 |
| 65 | Ph | H | H | OMe | OMe | H | 3NO₂-Ph | 3.37 | 70 | 447.26 |
| 66 | Ph | H | H | OMe | OMe | H | 4-NO₂Ph | 3.38 | 90 | 447.26 |
| 67 | Ph | H | H | OMe | OMe | H | 3-MePh | 3.54 | 75 | 416.29 |
| 68 | Ph | H | H | OMe | OMe | H | CH₂Ph | 3.44 | 85 | 416.29 |
| 69 | Ph | H | H | OMe | OMe | H | 3,5-(CF₃)₂Ph | 3.75 | 85 | 538.28 |
| 70 | Ph | H | H | OMe | OMe | H | 4-CF₃Ph | 3.58 | 80 | 470.25 |
| 71 | Ph | Ph | H | H | OMe | H | CH₂OPh | 3.79 | 70 | 478.3 |
| 72 | Ph | Ph | H | H | OMe | H | cBu | 3.8 | 95 | 426.31 |
| 73 | Ph | Ph | H | H | OMe | H | cHex | 3.93 | 73 | 454.34 |
| 74 | Ph | Ph | H | H | OMe | H | iPr | 3.82 | 90 | 414.44 |
| 75 | Ph | Ph | H | H | OMe | H | pentyl | 3.95 | 95 | 442.34 |

TABLE 2-continued

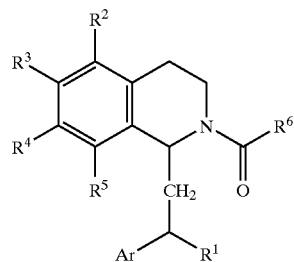

| Example | Ar | R¹ | R² | R³ | R⁴ | R⁵ | R⁶ | LC RT (min) | AP | MS (ES+) (M + H) |
|---|---|---|---|---|---|---|---|---|---|---|
| 76 | Ph | Ph | H | H | OMe | H | hexyl | 4.07 | 95 | 456.36 |
| 77 | Ph | Ph | H | H | OMe | H | nonyl | 4.69 | 95 | 498.43 |
| 78 | Ph | Ph | H | H | OMe | H | neopentyl | 3.89 | 95 | 442.34 |
| 79 | Ph | Ph | H | H | OMe | H | 4-MeOPh | 3.76 | 70 | 478.3 |
| 80 | Ph | Ph | H | H | OMe | H | 3-NO₂Ph | 3.72 | 80 | 493.29 |
| 81 | Ph | Ph | H | H | OMe | H | 4-NO₂Ph | 3.71 | 90 | 493.27 |
| 82 | Ph | Ph | H | H | OMe | H | 4-MePh | 3.85 | 78 | 462.28 |
| 83 | Ph | Ph | H | H | OMe | H | 3,5-(CF₃)₂Ph | 3.34 | 70 | 584.25 |
| 84 | 4-ClPh | Ph | H | OMe | OMe | H | Me | na | 100 | 450.98 |
| 85 | 4-ClPh | 4-ClPh | H | OMe | OMe | H | Me | na | 100 | 485.43 |
| 86 | 3-MeOPh | H | H | OMe | OMe | H | Me | na | 100 | 370.46 |
| 87 | 3-MeOPh | H | H | OMe | OMe | H | Et | na | 100 | 384.49 |
| 88 | 3-MeOPh | H | H | OMe | OMe | H | NHEt | na | 100 | 399.51 |
| 89 | Dihydrobenzfuran-4-yl | H | H | OMe | OMe | H | Me | 1.52 | 85 | 381 |
| 90 | 4-FPh | H | H | H | OMe | H | Me | 1.88 | 85 | 327.80 |
| 91 | Ph | Ph | H | OCH₂O | | H | Me | 1.84 | 100 | 400 |
| 92 | Ph | Ph | H | OCH₂O | | H | Pr | 1.95 | 90 | 414 |
| 93 | 4-FPh | H | H | OCH₂O | | H | Ph | 2.04 | 97 | 403.80 |
| 94 | 4-FPh | H | H | OCH₂O | | H | Me | 1.86 | 82 | 341.78 |
| 95 | 4-FPh | H | H | OCH₂O | | H | cPr | 1.96 | 91 | 367.77 |
| 96 | 4-FPh | H | H | OCH₂O | | H | CH₂OMe | 1.85 | 91 | 371.75 |
| 97 | 4-FPh | H | H | OCH₂O | | H | 4-MeOPh | 2.04 | 95 | 358.85 |
| 98 | 4-FPh | H | H | OCH₂O | | H | CH₂Cl | 1.91 | 93 | 375.71 |
| 99 | 4-FPh | H | H | OCH₂O | | H | OMe | 2.04 | 70 | 358.84 |
| 100 | 4-FPh | H | H | OCH₂O | | H | OCH₂Ph | 2.21 | 85 | 433.79 |
| 101 | 4-FPh | H | H | OCH₂O | | H | Pr | 2.01 | 83 | 369.77 |
| 102 | 4-FPh | H | H | OCH₂O | | H | cPentyl | 2.10 | 78 | 396.00 |
| 103 | 4-FPh | H | H | OCH₂O | | H | 5-isoxazolyl | 1.90 | 95 | 394.76 |
| 104 | 4-FPh | H | H | OCH₂O | | H | CH₂OAc | 1.83 | 94 | 399.76 |
| 105 | 4-FPh | H | H | OCH₂O | | H | Et | 1.93 | 87 | 355.78 |
| 106 | 4-FPh | H | H | OCH₂O | | H | OiBu | 2.22 | 83 | 399.82 |
| 107 | 4-FPh | H | H | OCH₂O | | H | neopentyl | 2.11 | 88 | 397.84 |
| 108 | 4-FPh | H | H | OCH₂O | | H | cinnamyl | 2.12 | 84 | 429.82 |
| 109 | 4-FPh | H | H | H | OMe | H | cPr | 1.98 | 87 | 353.81 |
| 110 | 4-FPh | H | H | H | OMe | H | CH₂OMe | 1.86 | 90 | 357.77 |
| 111 | 4-FPh | H | H | H | OMe | H | 4-MeOPh | 2.06 | 88 | 419.85 |
| 112 | 4-FPh | H | H | H | OMe | H | CH₂Cl | 1.93 | 89 | 362.00 |
| 113 | 4-FPh | H | H | H | OMe | H | OMe | 2.05 | 82 | 343.76 |
| 114 | 4-FPh | H | H | H | OMe | H | OCH₂Ph | 2.22 | 94 | 419.84 |
| 115 | 4-FPh | H | H | H | OMe | H | Pr | 2.03 | 89 | 355.80 |
| 116 | 4-FPh | H | H | H | OMe | H | cPentyl | 2.12 | 82 | 381.84 |
| 117 | 4-FPh | H | H | H | OMe | H | 5-isoxazolyl | 1.92 | 75 | 380.78 |
| 118 | 4-FPh | H | H | H | OMe | H | CH₂OAc | 1.85 | 96 | 385.85 |
| 119 | 4-FPh | H | H | H | OMe | H | Et | 1.95 | 84 | 341.83 |
| 120 | 4-FPh | H | H | H | OMe | H | OiBu | 2.23 | 81 | 385.83 |
| 121 | 4-FPh | H | H | H | OMe | H | neopentyl | 2.13 | 91 | 383.87 |
| 122 | 4-FPh | H | H | H | OMe | H | cinnamyl | 2.13 | 76 | 415.85 |
| 123 | 4-FPh | H | H | CH₂CH₂O | | H | Ph | 2.04 | 91 | 402.00 |
| 124 | 4-FPh | H | H | CH₂CH₂O | | H | Me | 1.87 | 75 | 339.78 |
| 125 | 4-FPh | H | H | CH₂CH₂O | | H | cPr | 1.98 | 78 | 366.00 |
| 126 | 4-FPh | H | H | CH₂CH₂O | | H | CH₂OMe | 1.86 | 91 | 369.77 |
| 127 | 4-FPh | H | H | CH₂CH₂O | | H | 4-MeOPh | 2.06 | 76 | 431.83 |
| 128 | 4-FPh | H | H | CH₂CH₂O | | H | CH₂Cl | 1.92 | 85 | 375.00 |
| 129 | 4-FPh | H | H | CH₂CH₂O | | H | OMe | 2.04 | 87 | 355.75 |
| 130 | 4-FPh | H | H | CH₂CH₂O | | H | Pr | 2.02 | 70 | 367.81 |
| 131 | 4-FPh | H | H | CH₂CH₂O | | H | cPentyl | 2.11 | 75 | 393.00 |
| 132 | 4-FPh | H | H | CH₂CH₂O | | H | 5-isoxazolyl | 1.90 | 85 | 392.78 |
| 133 | 4-FPh | H | H | CH₂CH₂O | | H | CH₂OAc | 1.84 | 88 | 397.80 |
| 134 | 4-FPh | H | H | CH₂CH₂O | | H | Et | 1.94 | 79 | 353.79 |
| 135 | 4-FPh | H | H | CH₂CH₂O | | H | OiBu | 2.23 | 78 | 397.82 |
| 136 | 4-FPh | H | H | CH₂CH₂O | | H | neopentyl | 2.13 | 81 | 395.86 |

TABLE 2-continued

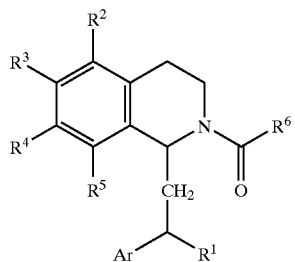

| Example | Ar | R¹ | R² | R³ | R⁴ | R⁵ | R⁶ | LC RT (min) | AP | MS (ES+) (M + H) |
|---|---|---|---|---|---|---|---|---|---|---|
| 137 | 4-ClPh | H | H | | OCH₂O | H | Ph | 2.12 | 90 | 419.78 |
| 138 | 4-ClPh | H | H | | OCH₂O | H | Me | 1.97 | 83 | 358.00 |
| 139 | 4-ClPh | H | H | | OCH₂O | H | cPr | 2.06 | 84 | 384.00 |
| 140 | 4-ClPh | H | H | | OCH₂O | H | CH₂OMe | 1.96 | 85 | 388.00 |
| 141 | 4-ClPh | H | H | | OCH₂O | H | 4-MeOPh | 2.13 | 90 | 450.00 |
| 142 | 4-ClPh | H | H | | OCH₂O | H | CH₂Cl | 2.01 | 77 | 393.00 |
| 143 | 4-ClPh | H | H | | OCH₂O | H | OCH₂Ph | 2.29 | 80 | 450.00 |
| 144 | 4-ClPh | H | H | | OCH₂O | H | Pr | 2.10 | 85 | 386.00 |
| 145 | 4-ClPh | H | H | | OCH₂O | H | 5-isoxazolyl | 1.99 | 94 | 411.00 |
| 146 | 4-ClPh | H | H | | OCH₂O | H | CH₂OAc | 1.93 | 92 | 416.00 |
| 147 | 4-ClPh | H | H | | OCH₂O | H | Et | 2.04 | 84 | 372.00 |
| 148 | 4-ClPh | H | H | | OCH₂O | H | OiBu | 2.30 | 70 | 416.00 |
| 149 | 4-ClPh | H | H | | OCH₂O | H | neopentyl | 2.20 | 77 | 414.00 |
| 150 | 4-ClPh | H | H | | OCH₂O | H | cinnamyl | 2.20 | 96 | 446.00 |

We claim:

1. A compound of Formula I

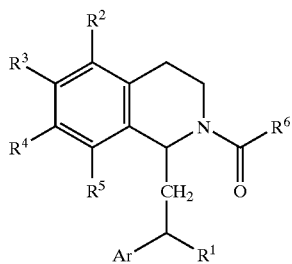

wherein

Ar is phenyl optionally substituted with 1–3 substituents selected from the group consisting of halogen, $C_{1-6}$alkyl, and $C_{1-6}$alkoxy, or Ar is 2,3-dihydrobenzfuran-4-yl;

$R^1$ is $C_{1-6}$alkyl or phenyl wherein phenyl is optionally substituted with 1–3 substituents selected from the group consisting of halogen, $C_{1-6}$alkyl, and $C_{1-6}$alkoxy;

or Ar and R taken together with the carbon to which they are attached are 1-indanyl or 9-fluorenyl;

$R^2$, $R^3$, $R^4$, and $R^5$ are independently hydrogen, halo, $C_{1-3}$alkoxy, or $C_{1-6}$alkyl;

or $R^2$ and $R^3$ taken together, $R^3$ and $R^4$ taken together, or $R^4$ and $R^5$ taken together are —O(CH₂)₂₋₃— or —O(CH₂)₁₋₂O—;

$R^6$ is selected from the group consisting of hydrogen, $C_{1-9}$alkyl, $C_{3-7}$cycloalkyl, $C_{1-6}$alkoxy, $C_{1-2}$perfluoroalkyl, —CH₂OC₁₋₃alkyl, —(CH₂)₁₋₂CO₂R⁷, —(CH₂)₁₋₂CO₂NR⁷₂, —NR⁷₂, —CH₂Cl, —CH₂OCOMe, —CH₂OPh, benzyl, 2-thienyl, 2-furanyl, 5-isoxazolyl, 4-biphenyl, naphthyl, 4-(1,2-methylenedioxy)phenyl, and phenyl where phenyl is optionally substituted with 1–3 substituents selected from halogen, $C_{1-3}$alkoxy, $C_{1-2}$perfluoroalkyl, $C_{1-2}$perfluoroalkoxy, and nitro; and $R^7$ is hydrogen or $C_{1-6}$alkyl;

or a stereoisomer, pharmaceutically acceptable salt, or solvate thereof.

2. The compound of claim 1 where Ar and $R^1$ are each phenyl optionally substituted with 1–3 substituents selected from halogen, $C_{1-6}$alkyl, and $C_{1-6}$alkoxy.

3. The compound of claim 2 where Ar is phenyl or 4-chlorophenyl and $R^1$ is phenyl.

4. The compound of claim 3 where $R^4$ is $C_{1-3}$ alkoxy.

5. The compound of claim 4 selected from the group consisting of 1-(2,2-diphenyl-ethyl)-6,7-dimethoxy-3,4-dihydro-1H-isoquinoline-2-carbaldehyde;

1-[1-(2,2-diphenyl-ethyl)-6,7-dimethoxy-3,4-dihydro-1H-isoquinolin-2-yl]-ethanone;

1-[1-(2,2-diphenyl-ethyl)-6-bromo-7-methoxy-3,4-dihydro-1H-isoquinolin-2-yl]-ethanone;

1-[1-(2,2-diphenyl-ethyl)-6-bromo-7-methoxy-3,4-dihydro-1H-isoquinolin-2-yl]-heptanone;

1-[1-(2-(4-chlorophenyl)-2-phenyl-ethyl)-6,7-dimethoxy-3,4-dihydro-1H-isoquinolin-2-yl]-ethanone;

1-[1-(2,2-diphenyl-ethyl)-6,7-dimethoxy-3,4-dihydro-1H-isoquinolin-2-yl]-propan-1-one;

1-[1-(2,2-diphenyl-ethyl)-6,7-dimethoxy-3,4-dihydro-1H-isoquinolin-2-yl]-butan-1-one;

cyclopropyl-[1-(2,2-diphenyl-ethyl)-6,7-dimethoxy-3,4-dihydro-1H-isoquinolin-2-yl]-methanone;

[1-(2,2-diphenyl-ethyl)-6,7-dimethoxy-3,4-dihydro-1H-isoquinolin-2-yl]-phenyl-methanone;

1-[1-(2,2-diphenyl-ethyl)-6,7-dimethoxy-3,4-dihydro-1H-isoquinolin-2-yl]-2,2,2-trifluoro-ethanone;

1-(2,2-diphenyl-ethyl)-6,7-dimethoxy-3,4-dihydro-1H-isoquinoline-2-carboxylic acid amide;

1-(2,2-diphenyl-ethyl)-6,7-dimethoxy-3,4-dihydro-1H-isoquinoline-2-carboxylic acid methylamide;

1-(2,2-diphenyl-ethyl)-6,7-dimethoxy-3,4-dihydro-1H-isoquinoline-2-carboxylic acid methyl ester; and 1-[1-(2,2-diphenyl-ethyl)-7-methoxy-3,4-dihydro-1H-isoquinolin-2-yl]-ethanone;

or a pharmaceutically acceptable salt or solvate thereof.

6. The compound of claim 3 where $R^3$ and $R^4$ taken together are —O(CH$_2$)$_{2-3}$— or —O(CH$_2$)$_{1-2}$O—.

7. A method of treating sleep disorders comprising the administration of a therapeutic amount of a compound of Formula Ia

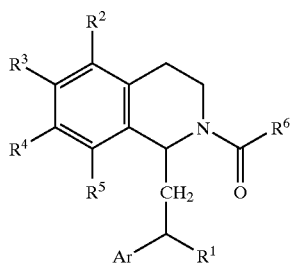

where:

Ar is phenyl optionally substituted with 1–3 substitutes selected from the group consisting of halogen, $C_{1-6}$alkyl, and $C_{1-6}$alkoxy, or Ar is 2,3-dihydrobenzfuran-4-yl;

$R^1$ is hydrogen, $C_{1-6}$alkyl, or phenyl wherein phenyl is optionally substituted with 1–3 substituents selected from the group consisting of halogen, $C_{1-6}$alkyl, and $C_{1-6}$alkoxy;

or Ar and R taken together with the carbon to which they are attached are 1-indanyl or 9-fluorenyl;

$R^2$, $R^3$, $R^4$, and $R^5$ are independently hydrogen, halo, $C_{1-6}$alkoxy, or $C_{1-6}$alkyl;

or $R^2$ and $R^3$ taken together, $R^3$ and $R^4$ taken together, or $R^4$ and $R^6$ taken together are —O(CH$_2$)$_{2-5}$— or —O(CH$_2$)$_{1-2}$O—;

$R^6$ is selected from hydrogen, $C_{1-8}$alkyl, $C_{3-7}$cycloalkyl, $C_{1-6}$alkoxy, $C_{1-2}$perfluoroalkyl, —CH$_2$OC$_{1-3}$alkyl, —(CH$_2$)$_{1-2}$CO$_2$R$^7$, —(CH$_2$)$_{1-2}$CO$_2$NR$^7{}_2$, —NR$^7{}_2$, —CH$_2$Cl, —CH$_2$OCOMe, —CH$_2$OPh, benzyl, 2-thienyl, 2-furanyl, 6-isoxazolyl, 4-biphenyl, naphthyl, 4-(1,2-methylenedioxy)phenyl, and phenyl wherein phenyl is optionally substituted with 1–3 substituents selected from the group consisting of halogen, $C_{1-3}$alkoxy, $C_{1-2}$perfluoroalkyl, $C_{1-2}$perfluoroalkoxy, and nitro; and $R^7$ is hydrogen or $C_{1-6}$alkyl;

or a stereoisomer, pharmaceutically acceptable salt, or solvate thereof.

8. A composition useful for treating a patient having sleep disorders comprising a therapeutic amount of a compound of claim 7 and a pharmaceutically acceptable carrier.

* * * * *